United States Patent
Park et al.

(10) Patent No.: US 9,892,248 B2
(45) Date of Patent: Feb. 13, 2018

(54) REFRIGERATOR AND METHOD FOR MEASURING BODY COMPOSITION USING THE REFRIGERATOR

(71) Applicant: Samsung Electronics Co., Ltd., Gyeonggi-do (KR)

(72) Inventors: Jong-won Park, Gyeonggi-do (KR); Hiroshi Awata, Gyeonggi-do (KR); Kwan-joon Kim, Gyeonggi-do (KR); Hyun-ki Kim, Gyeonggi-do (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/092,546

(22) Filed: Apr. 6, 2016

(65) Prior Publication Data
US 2016/0292409 A1    Oct. 6, 2016

(30) Foreign Application Priority Data

Apr. 6, 2015  (KR) .................. 10-2015-0048304

(51) Int. Cl.
| | |
|---|---|
| *G06F 21/32* | (2013.01) |
| *F25D 29/00* | (2006.01) |
| *A61B 3/00* | (2006.01) |
| *A61B 5/04* | (2006.01) |
| *F25D 15/00* | (2006.01) |
| *F25D 23/02* | (2006.01) |
| *A61B 5/00* | (2006.01) |
| *A61B 5/1172* | (2016.01) |
| *A61B 5/053* | (2006.01) |

(Continued)

(52) U.S. Cl.
CPC .......... *G06F 21/32* (2013.01); *A61B 5/0537* (2013.01); *A61B 5/1172* (2013.01); *A61B 5/4869* (2013.01); *A61B 5/6825* (2013.01); *A61B 5/6887* (2013.01); *A61B 5/749* (2013.01); *A61B 5/7475* (2013.01); *F25D 23/028* (2013.01); *F25D 29/005* (2013.01); *G06F 19/321* (2013.01); *A61B 3/0041* (2013.01); *A61B 3/028* (2013.01); *A61B 5/742* (2013.01); *F25D 2400/361* (2013.01); *F25D 2700/04* (2013.01)

(58) Field of Classification Search
CPC .......... G06F 21/32; F25D 29/00; G09D 19/00; A61B 5/1172; A61B 3/00; A61B 5/00
USPC ........... 340/5.83; 600/300, 372, 547; 62/331
See application file for complete search history.

(56) References Cited

U.S. PATENT DOCUMENTS

| | | | |
|---|---|---|---|
| 6,068,378 A | 5/2000 | Weiss | |
| 6,280,396 B1 * | 8/2001 | Clark | A61B 5/0537 |
| | | | 600/547 |

(Continued)

FOREIGN PATENT DOCUMENTS

| | | |
|---|---|---|
| JP | 2002531152 A | 9/2002 |
| JP | 2007143665 A | 6/2007 |

(Continued)

*Primary Examiner* — Nam V Nguyen

(57) ABSTRACT

A refrigerator includes a handgrip arranged on one side of a door to open and close a storage compartments, a measurer configured to measure fingerprints and body composition of a user when the user grabs the handgrip, a display configured to display the measured body composition information, and a controller configured to recognize the user based on the measured fingerprints and store the measured body composition information as information regarding the recognized user.

17 Claims, 17 Drawing Sheets

(51) Int. Cl.
*G06F 19/00* (2018.01)
*A61B 3/028* (2006.01)

(56) References Cited

U.S. PATENT DOCUMENTS

| | | | | |
|---|---|---|---|---|
| 6,733,131 | B1* | 5/2004 | Weiss | A61B 3/02 351/223 |
| 7,017,359 | B2* | 3/2006 | Kim | F25D 29/00 62/127 |
| 8,047,988 | B2* | 11/2011 | Lee | F25D 29/00 348/208.15 |
| 8,584,486 | B1* | 11/2013 | Allard | A23L 3/3418 62/377 |
| 2003/0135336 | A1* | 7/2003 | Inoue | A61B 5/0537 702/57 |
| 2004/0171464 | A1* | 9/2004 | Ashby | A63B 22/00 482/54 |
| 2005/0080353 | A1* | 4/2005 | Whang | A61B 5/0537 600/547 |
| 2006/0064298 | A1* | 3/2006 | Lee | G06F 3/04897 704/200 |
| 2006/0217600 | A1* | 9/2006 | Lee | F25D 23/12 600/300 |
| 2008/0184719 | A1* | 8/2008 | Lowenstein | F25D 29/00 62/127 |
| 2009/0204018 | A1* | 8/2009 | Tseng | A61B 5/0537 600/547 |
| 2015/0232320 | A1* | 8/2015 | Wait | F25D 31/005 165/200 |

FOREIGN PATENT DOCUMENTS

| | | |
|---|---|---|
| KR | 0141739 B1 | 6/1998 |
| KR | 19980028497 | 7/1998 |
| KR | 100484814 B1 | 4/2005 |
| KR | 20060026338 A | 3/2006 |
| KR | 20060042541 A | 5/2006 |
| KR | 20060054625 A | 5/2006 |
| KR | 100618265 B1 | 9/2006 |
| KR | 100681593 B1 | 2/2007 |
| KR | 20070027284 A | 3/2007 |
| KR | 20100121214 A | 11/2010 |
| KR | 101151056 B1 | 6/2012 |
| KR | 20120086536 A | 8/2012 |
| KR | 101266905 B1 | 5/2013 |
| KR | 20130061573 A | 6/2013 |
| KR | 20140098723 A | 8/2014 |

* cited by examiner

FIG. 11A

```
BODY FAT MEASURING MODE
    BODY INFORMATION
   No.      005     ▲▼
HEIGHT(cm)  170     △▽
WEIGHT(Kg)  60      △▽
   AGE      20      △▽
MALE/FEMALE MALE    △▽
   SET    ◁  ▷   CANCEL
```

FIG. 11B

```
BODY FAT MEASURING MODE
    BODY INFORMATION
   No.      004     ▲▼
HEIGHT(cm)  170     △▽
WEIGHT(Kg)  60      △▽
   AGE      20      △▽
MALE/FEMALE MALE    △▽
   SET    ◁  ▷   CANCEL
```

FIG. 11C

```
BODY FAT MEASURING MODE
    BODY INFORMATION
   No.      006     ▲▼
HEIGHT(cm)  170     △▽
WEIGHT(Kg)  60      △▽
   AGE      20      △▽
MALE/FEMALE MALE    △▽
   SET    ◁  ▷   CANCEL
```

FIG. 11D

```
BODY FAT MEASURING MODE
    BODY INFORMATION
   No.      005     △▽
HEIGHT(cm)  170     ▲▼
WEIGHT(Kg)  60      △▽
   AGE      20      △▽
MALE/FEMALE MALE    △▽
   SET    ◁  ▷   CANCEL
```

FIG. 11E

```
BODY FAT MEASURING MODE
    BODY INFORMATION
   No.      005     △▽
HEIGHT(cm)  183     ▲▼
WEIGHT(Kg)  60      △▽
   AGE      20      △▽
MALE/FEMALE MALE    △▽
   SET    ◁  ▷   CANCEL
```

FIG. 11F

```
BODY FAT MEASURING MODE
    BODY INFORMATION
   No.      005     △▽
HEIGHT(cm)  153     ▲▼
WEIGHT(Kg)  60      △▽
   AGE      20      △▽
MALE/FEMALE MALE    △▽
   SET    ◁  ▷   CANCEL
```

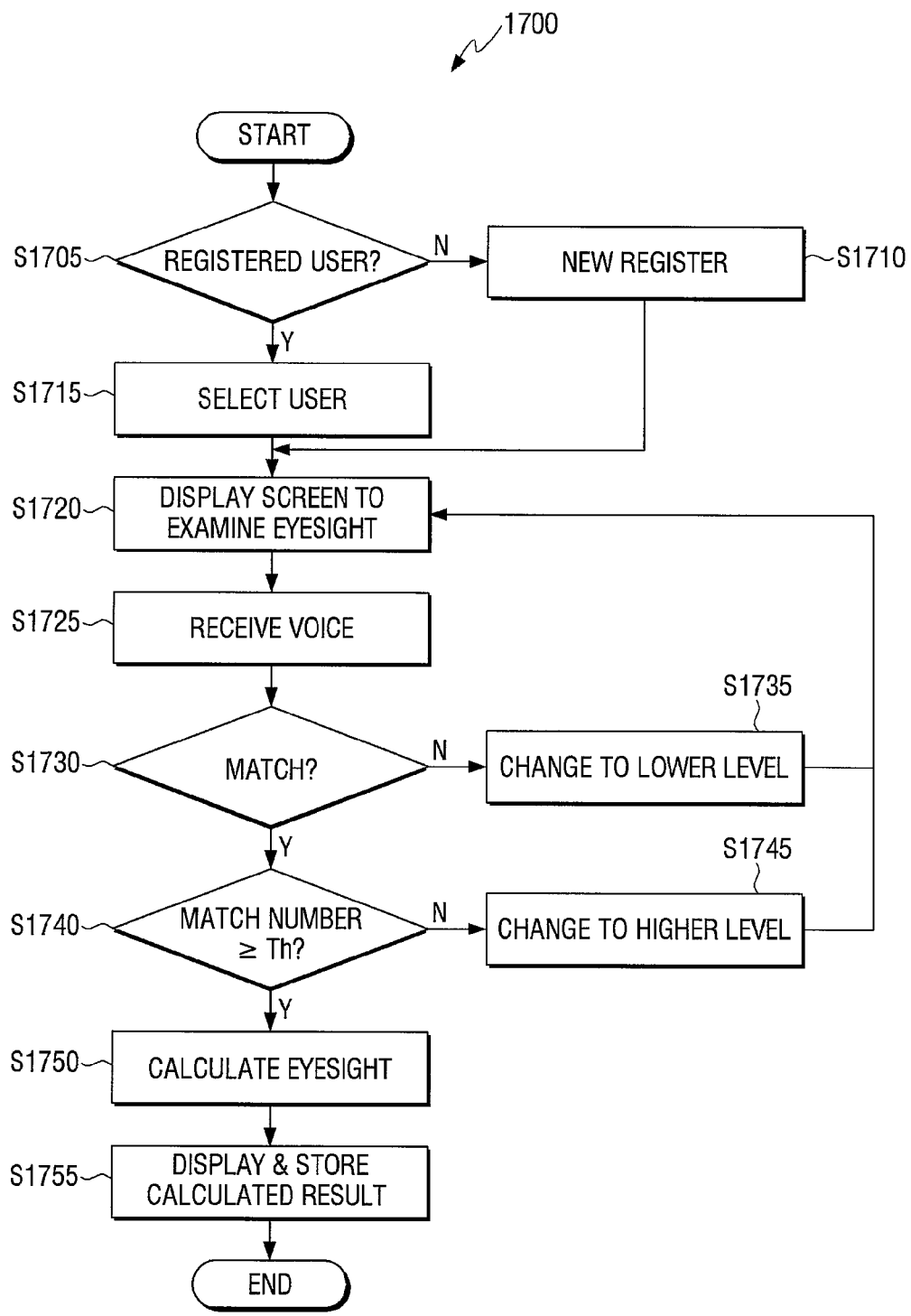

REFRIGERATOR AND METHOD FOR MEASURING BODY COMPOSITION USING THE REFRIGERATOR

CROSS-REFERENCE TO RELATED APPLICATION AND CLAIM OF PRIORITY

The present application is related to and claims benefit from Korean Patent Application No. 10-2015-0048304, filed on Apr. 6, 2015 in the Korean Intellectual Property Office, the disclosure of which is incorporated herein by reference in its entirety.

TECHNICAL FIELD

Apparatuses and methods consistent with what is disclosed herein relate to a refrigerator and a method for measuring body composition, and more specifically, to a refrigerator configured to measure body composition and fingerprints of a user and a method for measuring body composition using the refrigerator.

BACKGROUND

Generally, a refrigerator refers to a device which keeps the internal storage compartments at a low temperature in order to preserve the foods fresh for a long time. The refrigerator is recently developing to support more various functions with the above-described use, such as to store the foods. Specifically, the refrigerator is a home appliance used widely at home, and expanding of the functions implemented by the refrigerator can enrich the quality of the life for more users. Further, as the interests in the health of the modern living increase, a user may show increasing demands regarding functions to manage the health of a user in addition to store and eat the foods benefited for the body in the refrigerator.

SUMMARY

To address the above-discussed deficiencies, it is a primary object to provide a refrigerator which measures body composition and fingerprints of a user and a method for measuring body composition thereof.

According to an embodiment, a refrigerator is provided. The refrigerator may include a handgrip arranged on one side of a door to open and close a storage compartment. The refrigerator also may include a measurer configured to measure fingerprints and body composition regarding a user when the user grabs the handgrip. The refrigerator may further include a display configured to display the measured body composition. The refrigerator may include a controller configured to recognize the user based on the measured fingerprints and store the measured body composition as information regarding the recognized user on a storage. The measurer may include a fingerprint sensor configured to recognize fingerprints, and a body composition measurer configured to measure body composition of the user contacting a pair of electrodes.

The fingerprint sensor may be provided with a contact surface to recognize a fingerprint of a thumb within an operating range where a thumb of the grabbing hand can reach the handgrip, when the user grabs the handgrip. The body composition measurer may be provided with a pair of electrodes respectively spanning the portions of the handgrip in contact with the palms of the both hands, when the user grabs the handgrip with his or her both hands. The refrigerator may be a side by side door (SBS) type, the handgrip may be respectively provided on the both side doors, and a pair of the electrodes may be arranged on the both handgrips so as to be contacted respectively by the both hands grabbing the handgrips of the side doors.

The controller may control the body composition measurer to start measuring the body composition, when recognizing the fingerprints is continued for a predetermined time by the fingerprint sensor. The controller may control the measurer to measure the body composition when prestored identification information regarding the user corresponding to the measured fingerprints is searched. The measurer may measure the impedance of the hand by outputting alternated currents to the hand of the user grabbing the handgrip, and the controller may determine whether or not the user grabs the handgrip in properly based on the measured size of the impedance. The measurer may additionally include a power source configured to provide alternated currents to measure the body composition, and a switching unit configured to switch connection to a pair of the electrodes outputting the provided alternated currents externally, to other electrodes.

The controller may control so that options provided to the user are selected according to patterns of a signal of the fingerprints being recognized by the fingerprint sensor. The controller may control so that options provided to the user are selected according to pattern of impedance in which the impedance of the hand contacting at least one among the pair of the electrodes in the body composition measurer changes. The storage may additionally store additional information comprising at least one among age, gender, height and weight regarding a plurality of users. The controller may search additional information corresponding to the recognized user among a plurality of pieces of the stored additional information. The measurer may measure the body composition of the user by considering the searched additional information. The display may display characters to examine eyesight of the user. The refrigerator may additionally include an inputter configured to receive a user voice. The controller may change the character displayed on the display according to whether the received voice corresponds to the displayed character.

In an embodiment, a method for measuring body composition is provided. The method may include recognizing fingerprints from a hand of a user grabbing a handgrip arranged on one side of a door to open and close a storage compartment of a refrigerator. The method also may include recognizing the user based on the recognized fingerprints. The method may further include measuring the body composition of the user by using a pair of electrodes contacting both hands of the user grabbing the handgrip. The method may include storing the measured body composition information as information regarding the recognized user. The measuring the body composition may include measuring the body composition of the user, when the recognizing the fingerprints is continued for a predetermined time.

The measuring the body composition may include measuring the body composition of the user, when prestored identification information of the user corresponding to the recognized fingerprints is searched. The method may additionally include switching a connection of a power source providing the alternated currents to measure the body composition with a pair of electrodes outputting the provided alternated current externally, to connection with other electrodes. The method may additionally include previously storing additional information comprising at least one among age, gender, height, and weight regarding a plurality of users, and searching additional information corresponding to the recognized user among a plurality of pieces of the stored additional information. The measuring the body composition may include analyzing the body composition of the user by considering the searched additional information. The method may additionally include displaying a character to examine eyesight of the user, receiving user voice, and changing the displayed character according to whether or not the received voice corresponds to the displayed character.

According to the above various embodiments, more convenient managing the user body measuring information can be performed. Further, dimensional economic feature can be obtained within the house because another body measuring device may not be requested. Further, manipulation can be performed while grabbing the handgrip without providing another inputting device. Further, complicated feature of the circuit can be reduced and the cost can be saved with the constitution to switch the connection with the electrical source. The eye health that may be often ignored can be easily managed by using the refrigerator having good approaches.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIGS. 11A, 11B, 11C, 11D, 11E, and 11F are diagrams illustrating examples in which screens are changed by user manipulation inputted according to this disclosure;

FIG. 17 is an example method for measuring body composition according to this disclosure.

DETAILED DESCRIPTION

Figure 1:
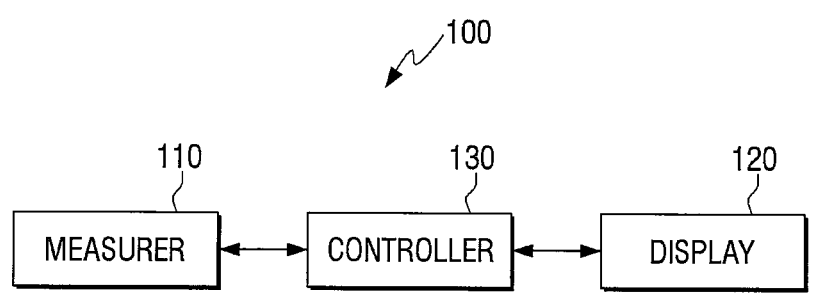
FIG. 1 is a block diagram of an example refrigerator according to this disclosure.

FIGS. 1 through 17, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged electronic device, refrigeration unit, or refrigeration system. Certain exemplary embodiments of the present inventive concept will now be described in greater detail with reference to the accompanying drawings.

The exemplary embodiments of the present disclosure may be diversely modified. Accordingly, specific exemplary embodiments are illustrated in the drawings and are described in detail in the detailed description. However, it is to be understood that the present disclosure is not limited to a specific exemplary embodiment, but includes all modifications, equivalents, and substitutions without departing from the scope and spirit of the present disclosure. Also, well-known functions or constructions are not described in detail since they would obscure the disclosure with unnecessary detail. The terms "first", "second", etc. may be used to describe diverse components, but the components are not limited by the terms. The terms are only used to distinguish one component from the others.

The terms used in the present application are only used to describe the exemplary embodiments, but are not intended to limit the scope of the disclosure. The singular expression also includes the plural meaning as long as it does not differently mean in the context. In the present application, the terms "include" and "consist of" designate the presence of features, numbers, steps, operations, components, elements, or a combination thereof that are written in the specification, but do not exclude the presence or possibility of addition of one or more other features, numbers, steps, operations, components, elements, or a combination thereof.

In the exemplary embodiment of the present disclosure, a "module" or a "unit" performs at least one function or operation, and may be implemented with hardware, software, or a combination of hardware and software. In addition, a plurality of "modules" or a plurality of "units" may be integrated into at least one module except for a "module" or a "unit" which has to be implemented with specific hardware, and may be implemented with at least one processor. Hereinafter, the present disclosure will be described in detail with reference to the accompanying drawings.

FIG. 1 is an example block diagram of a refrigerator according to this disclosure. Referring to FIG. 1, a refrigerator 100 includes a measurer 110, a display 120 and a controller 130. The refrigerator 100 may include one or a plurality of storage compartments which stores foods at the low temperature in a main body constituting the exterior thereof. Further, one, or a plurality of doors to open or close the storage compartments are provided. The refrigerator 100 also may provide a mechanic compartment so that the heat exchanging is performed between external air and internal air within the storage compartments by a heat exchanger of the mechanic compartment.

A handgrip may be arranged on one side of the door of the refrigerator 100. Specifically, the door to open or close the storage compartments may include the handgrip so that a user can grab with his or her hand. The handgrip may be configured in various shapes as far as it allows a user to grab it with his or her hand.

The measurer 110 measures user fingerprints and user body composition when a user grabs the handgrip. Specifically, the measurer 110 may measure fingerprints of the user's hand grabbing the handgrip. For the above, the measurer 110 may include a fingerprint sensor to recognize fingerprints. Further, the measurer 110 may include a body composition measurer including a pair of electrodes to measure body composition of the user who grabs. This will be further explained below by referring to FIG. 2.

The measurer 110 may measure body composition by considering additional information. Specifically, the measurer 110 may perform measuring body composition more correctly by considering the prestored additional information regarding the recognized user. Herein, the additional information may include at least one of the age, the gender, the height, and the weight of a user.

The measurer 110 may measure the impedance of the hand by outputting the alternated currents to the hand of a user grabbing the handgrip. Specifically, the measurer 110 may discharge the alternated currents to the hand of a user grabbing the handgrip through the two electrodes provided on the handgrip. Further, the measurer 110 may calculate the impedance of the hand by measuring the size of the outputting alternated currents and the voltage between the two electrodes.

The display 120 displays the measured body composition information. Specifically, the display 120 may visually display the measured body composition information in order to provide the measuring result to a user who requests the measuring body composition. The display 120 may display screens to provide various options and information that is selected as well as screens indicating the measured body composition information.

The display 120 may be implemented to be at least one among the liquid crystal display, the thin film transistor-liquid crystal display, the organic light-emitting diode, the flexible display and 3D display.

The controller 130 controls each component of the refrigerator 100. Specifically, the controller 130 may control operation of the components to perform body composition measuring function implemented in the refrigerator 100. Further, the controller 130 may include CPU, read-only memory (ROM) storing control programs for the controlling of the refrigerator 100, and random access memory (RAM) used as memory region for the record of signals or data inputted externally or the operation performed in the refrigerator 100. CPU may include at least one among the single core processor, the dual core processor, the triple core processor and the quad core processor. CPU, ROM and RAM may be connected to each other through an internal bus.

The controller 130 may recognize a user based on the fingerprints measured by the measurer 110. Specifically, the controller 130 may generate identification data that is recognized by the perspective of a user based on the fingerprint information when the user fingerprints are measured. Further, the controller 130 may store the measured body composition information in a storage unit. Specifically, the controller 130 may store the measured body composition information as information regarding the recognized user on the storage. For example, the controller 130 may store the information regarding the recognized user as identification information for the registered user on the storage, and the measured body composition related with the identification information on the storage. The body composition information stored on the storage may be accumulated to be stored, or renewed whenever being measured.

The storage may further store additional information. Specifically, the storage may store additional information regarding a plurality of users. Herein, the storage may be implemented to be storing medium within the refrigerator 100 and external storing medium, such as removable disk including USB memory and web server through network. Although the embodiment explains that RAM and ROM used for storing and performing controlling programs are components of the controller 130, they may be components of the storage.

The controller 130 may control the measurer 110 to measure body composition when prestored identification information corresponding to the measured fingerprints is searched. Specifically, when measuring fingerprints is performed, identification information corresponding to the measured fingerprints may be searched on the storage. When the identification information is searched, the controller 130 may control the measurer 110 to start the measuring body composition while considering a user to be previously registered. Differently from the above, when prestored identification information is not searched, the controller 130 may recognize a user to be newly registered, and start the registering a user on the storage.

The controller 130 may determine whether a user grabs the handgrip in properly based on the measured size of the impedance regarding the hand in the measurer 110. Specifically, the controller 130 may determine whether a user grabs the handgrip with a proper method to measure body composition by comparing a preset critical value with the measured impedance of the hand in the measurer 110. The controller 130 may search additional information corresponding to the recognized user on the storage. Specifically, the controller 130 may search identification information of the recognized user on the storage by using the measured fingerprints, and search additional information corresponding to the searched identification information. Further, the controller 130 may deliver the searched additional information to the measurer 110 so that the measuring body composition is performed by considering the additional information. As described above, the refrigerator can manage and store the measured body composition information corresponding to a user without requiring user's manipulation to search and select corresponding identification information, which can be inconvenient.

Figure 2:
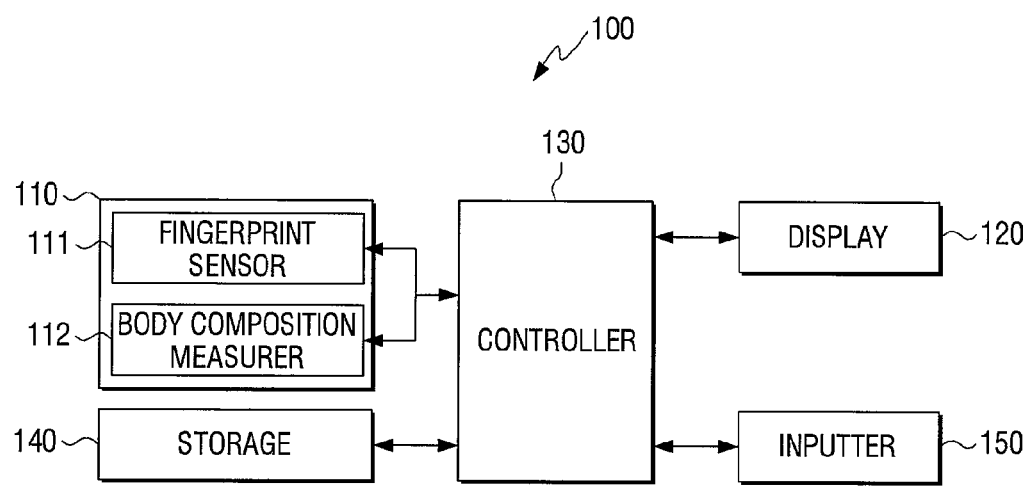
FIG. 2 is a block diagram of an example refrigerator according to this disclosure.

FIG. 2 is an example block diagram of a refrigerator according to this disclosure. Referring to FIG. 2, the refrigerator 100 includes the measurer 110 including the fingerprint sensor 111 and the body composition measurer 112, the display 120, the controller 130, the storage 140 and an inputter 150. Herein, the display 120, the controller 130 and the storage 140 include the constitution and the operation regarding the display 120, the controller 130, and the storage 140 in FIG. 1.

The fingerprint sensor 111 may recognize fingerprints. Specifically, the fingerprint sensor 111 may recognize fingerprints of the fingers regarding a user grabbing the handgrip. The fingerprint sensor 111 may be implemented to be various types of sensors. For example, the fingerprint sensor 111 may be optical fingerprint recognition sensor which generates reflective images based on the differences in reflectivity of the engraved ridges and valleys regarding the fingerprints, after total-reflection of the light emitted from the light source against the fingerprints with a lens and a prism. Further, the fingerprint sensor 111 may be a capacitive fingerprint recognition sensor which calculates capacitive amount of the engraved ridges and valleys regarding the fingerprints and implements the measured electrical signals as digital images. Further, the fingerprint sensor 111 may be a thermal fingerprint recognition sensor which uses pyroelectric materials sensing the temperature changes with the temperature differences of the engraved ridges and valleys regarding the fingerprints when the finger contacts, and generating electrical signals.

The fingerprint sensor 111 may be provided with contact surface to recognize the fingerprints of the thumb within the operating range in which the thumb of the grabbing hand can contact the handgrip when a user grabs the handgrip. Specifically, the fingerprint sensor 111 may be provided with the contact surface to recognize fingerprints of the user thumb on position where the fingerprints of the thumb can naturally touch when a user grabs the handgrip. The body composition measurer 112 may measure body composition of a user contacting the electrodes by including a pair of the electrodes. Specifically, the body composition measurer 112 may include a pair of the electrodes including four electrodes. Further, the four electrodes may be respectively including both sides to output the alternated currents and both-sided electrodes to measure the voltage.

The body composition measurer 112 may be provided to implement algorithms using the bio-electrical impedance analysis method (BIA). Specifically, the body composition measurer 112 may include the algorithms which flow the micro-electrical currents to the body and calculate body water, body fat, and lean mass which are compositions of the body from the measured body impedance. Further constitution of the body composition measurer 112 is described herein.

The body composition measurer 112 may be provided with a pair of the electrodes respectively crossing over the portions of the handgrip where the palms of the both hands touch when a user grabs the handgrip with his or her both hands. Specifically, a pair of the electrodes outputting the electrical currents of the body composition measurer 112 may be inserted within the handgrip, and parts of the electrodes may be exposed externally, which can contact both hands of a user grabbing the handgrip. Herein, when the refrigerator 100 is side by side door (SBS) type and the handgrip is respectively provided on each door, the electrodes of the body composition measurer 112 may be provided to be pair on each handgrip so that the electrodes respectively contact the both hands grabbing the handgrips of the two doors.

The storage 140 may store various implementing programs requested for the control and the operation of the refrigerator 100. Specifically, the storage 140 may store platforms to generate controlling commands regarding the hardware of the refrigerator 100, OS for driving the programs, and applications manufactured for the purpose of performing specific functions. The storage 140 may accumulate and store the health information of a user as records according to the time. The inputter 150 may receive user inputting. For example, the inputter 150 may be implemented to be buttons receiving pushing of a user or capacitive panel receiving touching of a user. Herein, the above describes that the inputter 150 is separate component for the interface of a user; however, the inputter 150 can be one touch screen panel with the display 120 in which touch inputting is performed on the screen, when being implemented.

The controller 130 may control the body composition measurer 112 to start the measuring body composition when recognizing fingerprints are continued for predetermined time in the fingerprint sensor 111. Specifically, the controller 130 may determine that a user is trying to measure body composition when the user manipulation to recognize fingerprints by the fingerprint sensor 111 is continued for predetermined time, and control the body composition measurer 112 to measure body composition by flowing the electrical currents to the both hands of a user grabbing the handgrip without another inputting manipulation.

The controller 130 may control options to be selected according to a command of the user manipulation. Specifically, the controller 130 may display options that are selected by a user through the display 120. Further, the controller 130 may control the selecting to be performed according to a command of the user manipulation corresponding to the displayed options. The controller 130 may receive signals in which the fingerprint sensor 111 recognizes fingerprints. Specifically, the controller 130 may receive signals to sense the contact on the contact surface to recognize fingerprints by the fingerprint sensor 111. Further, the controller 130 may control the options to be selected according to patterns of the signals in which the fingerprints are recognized.

Meanwhile, the controller 130 may control the options to be selected according to patterns in which the size of the impedance regarding the hand contacting at least one among a pair of the electrodes in the body composition measurer 112 changes. For example, the controller 130 may binary-code the size of the impedance which changes according to the situation of the hand grabbing the handgrip based on a preset quantization value, and control the options to be selected according to patterns in which the binary-coded value changes. The above described patterns for the user manipulation will be specifically explained by referring to FIGS. 8A, 8B, 9A, 9B, 10A, 10B, 10C, and 10D. As described herein, the refrigerator senses proper grabbing the handgrip to measure body composition without another constitution and select options only with the pattern operation such as grabbing the handgrip or touching without user inputting through another inputting device.

Figure 3:
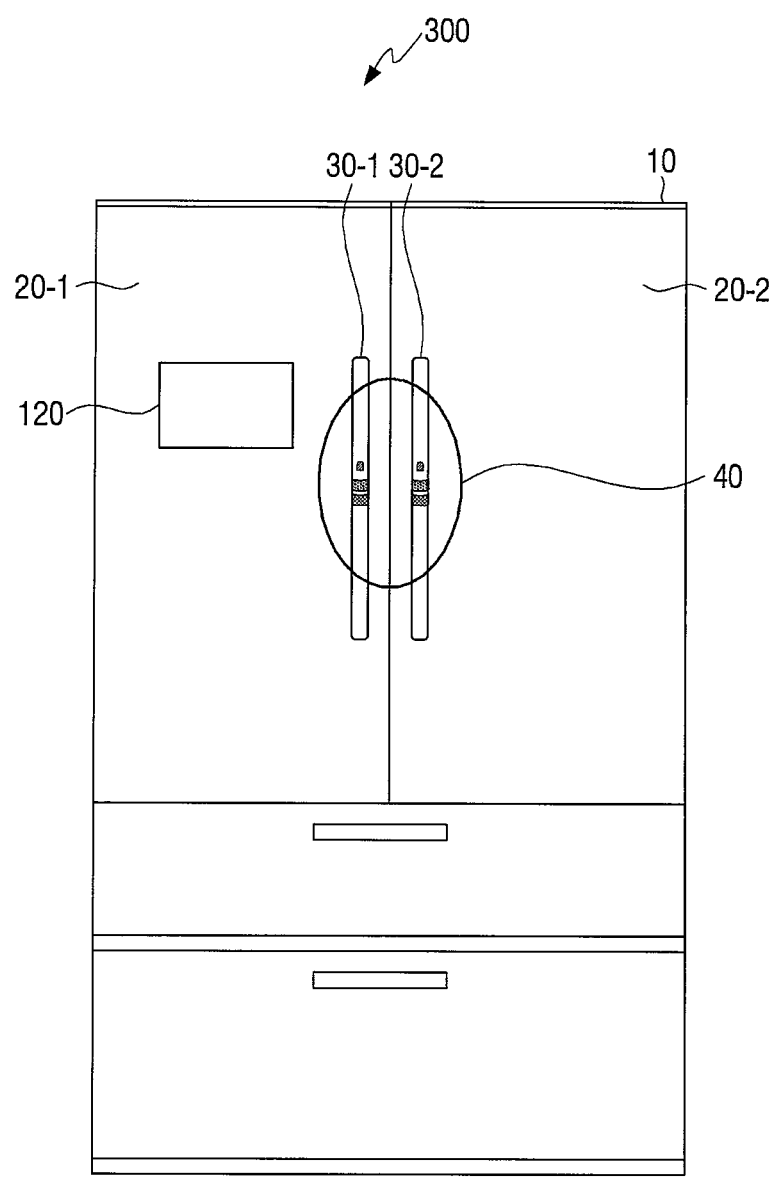
FIG. 3 illustrates an exterior of an example refrigerator according to this disclosure.

FIG. 3 illustrates an example exterior of the refrigerator according to this disclosure. Referring to FIG. 3, the refrigerator 300 includes a main body 10, the left and right doors 20-1, 20-2, the display 120, and the left and right handgrips 30-1, 30-2. The main body 10 of the refrigerator 100 forms the exterior, prevents the external shock, sections the storage compartments through partitions, blocks the external air, and includes insulating materials to keep the internal air at the low temperature. The refrigerator 300 includes the three storage compartments. The most upper storage compartments are provided with SBS type of doors in which the two doors are opened toward the left and right directions, and the lower two storage compartments are provided with the cabinet type of doors.

The left and right doors 20-1, 20-2 are respectively arranged with the handgrips 30-1, 30-2. Specifically, the left and right doors 20-1, 20-2 to open or close the upper storage compartments are respectively hinge-coupled with the most left and the most right of the main body, and the left and right handgrips 30-1, 30-2 are arranged on the center of the refrigerator when the doors 20-1, 20-2 are closed. The display 120 is arranged on the front of the refrigerator 300. Specifically, the display 120 is arranged on the exterior side of the doors 20-1, 20-2 so that a user watching the refrigerator 300 can view the screen.

Figure 4:
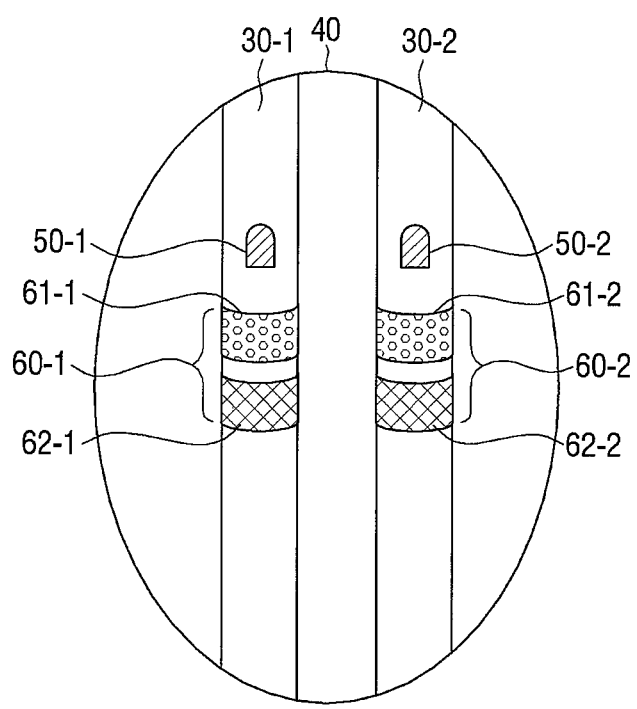
FIG. 4 is an enlarged view of a handgrip of a refrigerator according to this disclosure.

Referring to FIG. 4, constitution provided on the portion 40 of the handgrips 30-1, 30-2 where a user grabs is described. FIG. 4 is an enlarged view of the handgrips of a refrigerator such as the refrigerator of FIG. 3 according to this disclosure. Referring to FIG. 4, the contact surfaces 50-1, 50-2 and the electrodes 60-1, 60-2 are provided on the area 40 of the two handgrips 30-1, 30-2 which are arranged on the center of SBS type refrigerator 300 and respectively grabbed by a user. Further, a pair of the electrodes 60-1, 60-2 respectively includes the current electrodes 61-1, 61-2 and the voltage electrodes 62-1, 62-2.

According to an embodiment of FIG. 4, the handgrips 30-1, 30-2 have a cylindrical shape. When a user grabs the handgrips 30-1, 30-2 with his or her hand, the user's palm covers the outer circumference surface of the handgrips 30-1, 30-2, and the user's thumb stretches toward the length direction of the handgrips 30-1, 30-2 and pushes the handgrips 30-1, 30-2.

The contact surfaces 50-1, 50-2 and the electrodes 60-1, 60-2 are arranged according to the shape of the grabbing hand. The contact surfaces 50-1, 50-2 are arranged on the position in which the thumb fingerprints are recognized, and the electrodes 60-1, 60-2 are arranged on the position in which the electrical currents are conducted following to the both palms of a user and the voltage is measured. Further, the contact surfaces 50-1, 50-2 and the electrodes 60-1, 60-2 regarding the handgrips 30-1, 30-2 are arranged within the distance that a user can cover usually with his or her one hand.

Figure 5:
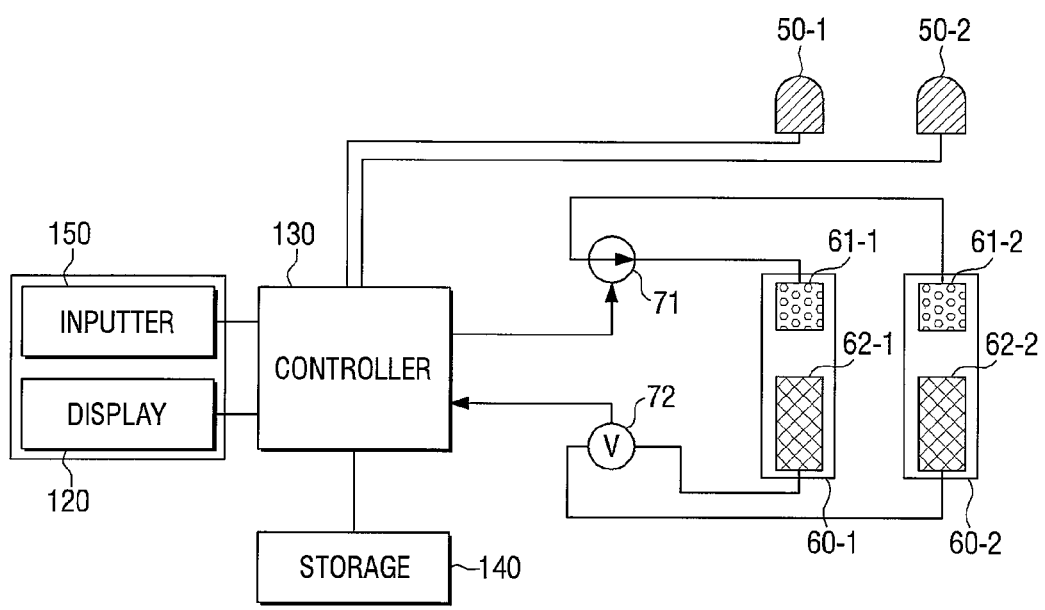
FIG. 5 is a circuit diagram of an example refrigerator according to this disclosure.

FIG. 5 is a circuit diagram of a refrigerator according to this disclosure. Referring to FIG. 5, the inputter 150 and the display 120 are exposed so that they can be approached by a user, and the internally equipped controller 130 and storage 140 are illustrated in a block diagram. Further, the fingerprint sensor 111 and the body composition measurer 112 of the measurer 110 are illustrated in a brief circuit diagram.

The signals recognizing the fingerprints and the digital images of the recognized fingerprints on the contact surfaces 50-1, 50-2 of the fingerprint sensor 111 is transmitted to the controller 130. The body composition measurer 112 includes the electrodes 60-1, 60-2, a power source 71, and a voltage measurer 72. The electrical power 71 provides the alternated currents according to a command to start the measuring body composition from the controller 130, and the provided alternated currents are outputted through the current electrodes 61-1, 61-2 connected to the outputting ends of the electrical power 71.

The outputting currents form the potential difference by passing through the user body following to the both hands of a user contacting a pair of the current electrodes 61-1, 61-2. The voltage measurer 72 measures the formed potential difference by being connected to a pair of the voltage electrodes 62-1, 62-2 contacting the both hands of a user.

Further, the voltage measurer 72 delivers the measured voltage to the controller 130. The controller 130 calculates the impedance by using the provided electrical currents and the measured potential difference. Further, the controller 130 calculates the body composition of a user by further considering the measured additional information of a user with the calculated impedance.

Although FIG. 5 describes that one controller 130 performs the calculation to measure the body composition, another processor is included in the measurer 110 and can be applied to the calculation for the measuring body composition when being implemented.

Figure 6:
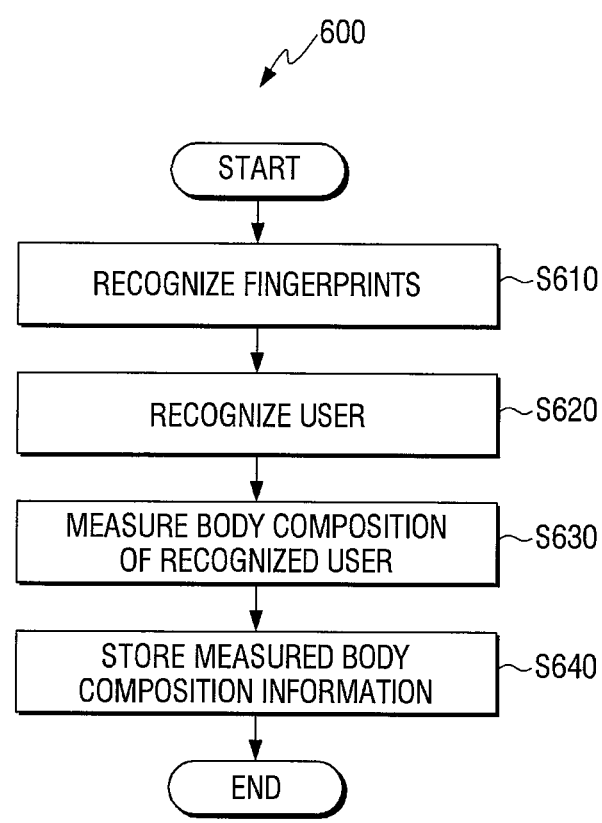
FIG. 6 is a flowchart of an example method for measuring body composition according to this disclosure.

FIG. 6 is an example flowchart describing a method 600 for measuring body composition according to this disclosure. Referring to FIG. 6, fingerprints are recognized from the user hand grabbing the handgrip arranged on one side of the doors to open or close the storage compartments of the refrigerator at S610. At S620, a user is recognized based on the recognized fingerprints. Specifically, a user may be recognized by creating identification information corresponding to unique features of the fingerprints or by searching the previously registered identification information of a user.

Further, body composition of a user is measured by using a pair of the electrodes contacting the both hands of a user grabbing the handgrip at S630. Specifically, body composition of a user may be measured by using the algorithms according to the bio-electrical impedance analysis method (BIA). At S640, the measured body composition information is stored as information regarding the recognized user. Specifically, the measured body composition information may be stored by corresponding to the identification information of a user who is measured.

As described herein, the body composition measuring method automatically recognizes a user with the refrigerator that is easily approached at home, and stores the measured body information. Thus, even when a plurality of users is utilized, the convenient health management is provided without repeated manipulation to select a user.

Further, the body composition measuring method according to an embodiment is implemented in the refrigerators illustrated in FIGS. 1 and 2. The body measuring method is implemented to be at least one program to perform the body measuring method, and such programs are stored in recording medium that can be read by a computer. Therefore, each block according to an embodiment is performed as codes that are recorded by a computer on the recording medium that can be read by a computer. The recording medium that is read by a computer is a device storing data that is read by the computer system.

For example, the recording medium that is read by a computer can be ROM, RAM, CD-ROMs, magnetic tapes, floppy disk, optical disk, optical data storing device, image display apparatus including the above storing devices such as TV, or the like. Further, the codes that are recorded by a computer are performed as computer data signals having carrier waves.

Figure 7A:
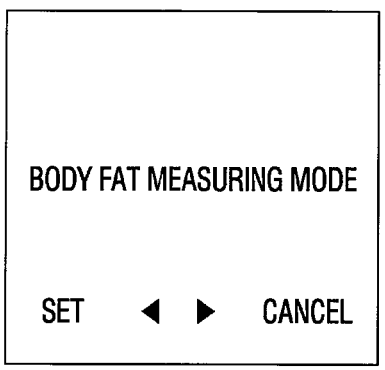
FIGS. 7A, 7B, 7C, and 7D are example screens provided to a user for measuring body composition by a refrigerator according to this disclosure.

FIGS. 7A, 7B, 7C, and 7D are example screens provided to a user for the measuring body composition in the refrigerator according to this disclosure. Referring to FIGS. 7A to 7D, the screen of FIG. 7A provides that a user checks whether to enter into the body fat measuring mode when the user fingerprints are recognized for predetermined time. When a user inputs a command to cancel with the user manipulation on the above screen, the refrigerator goes back to the normal mode. On the contrary, when a user inputs a command to determine the user manipulation, the screen of FIG. 7A is converted into the screen of FIG. 7B.

Figure 7B:
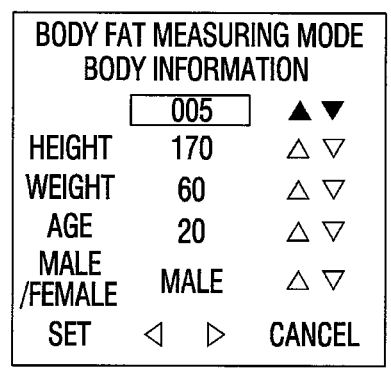

The screen of FIG. 7B provides that a user checks his or her additional information to be correct by displaying identification information corresponding to the recognized fingerprints. The example of FIG. 7B arranges the searched unique identification number to be 5 and the additional information such as height, weight, age, and gender based on the recognized fingerprints. A user determines the additional information on the screen or selects the cancel of the measuring body fat. When a user determines the additional information, the screen is converted into the screen of FIG. 7D.

Figure 7C:
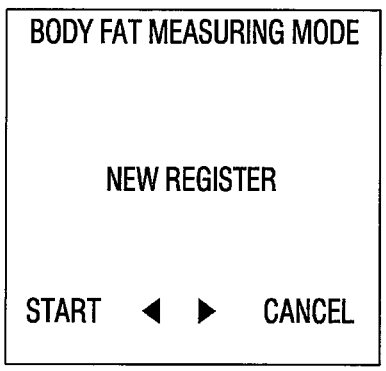
Figure 7D:
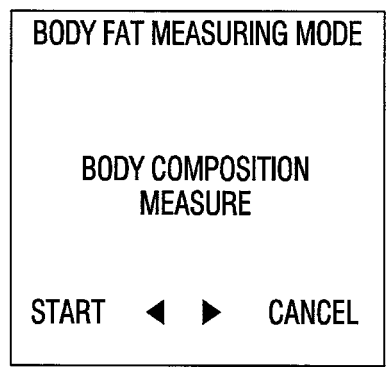

The screen of FIG. 7C provides the options when preregistered user information cannot be obtained from the recognized fingerprints. A user starts the new registering or cancels the measuring on the screen. The screen of FIG. 7D provides the start or the cancel of the measuring body fat. When a user selects the start, processes according to a BIA method is performed.

FIGS. 8A, 8B, 9A, 9B, 10A, 10B, 10C and 10D are graphs describing patterns that are manipulated by a user utilizing the handgrip in the refrigerator according to an embodiment. The examples of FIGS. 8A, 8B, 9A, 9B, 10A, 10B, 10C, and 10D are graphs regarding the signals indicating whether the fingerprints are sensed or graphs binary-coding the size of the impedance regarding the hands of a user grabbing the handgrip. Thus, when explaining FIGS. 8A, 8B, 9A, 9B, 10A, 10B, 10C, and 10D, the illustrated timing graphs are assumed to be examples of the patterns regarding the signals inputted through any one method among the two methods that a user manipulates on the grabbed handgrip. Further, the sections with hatching of the timing graphs are 'don't care' sections in which the signals are not considered to determine the patterns.

Figure 8A:
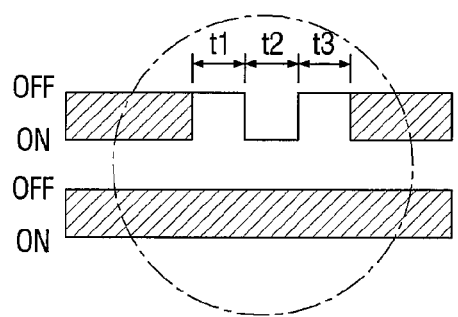
FIGS. 8A, 8B, 9A, 9B, 10A, 10B, 10C and 10D are graphs provided to explain patterns in which a user can manipulate with the handgrip of the refrigerator according to this disclosure.
Figure 8B:
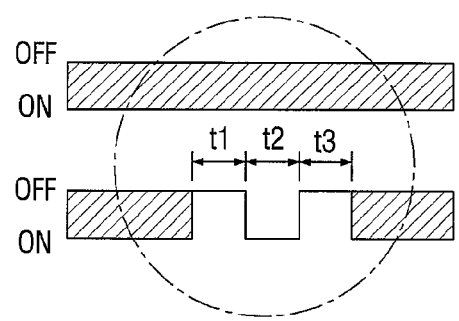

FIGS. 8A and 8B illustrate inputting patterns of the user manipulation to select any one when the two options that can be selected are provided to a user, such as when the two selections of the determining and the canceling are provided on the displayed screen. According to the above example, the determining is selected through the manipulation of the user left hand grabbing the handgrip in FIG. 8A, and the cancelling is selected through the manipulation of the user right hand grabbing the handgrip in FIG. 8B. Further, after entering into the process determining the patterns, the time sections t1 and t3 are previously defined to be more than 0.5 seconds, and t2 is previously defined to be more than 0.3 seconds and less than 0.8 seconds.

Figure 9A:
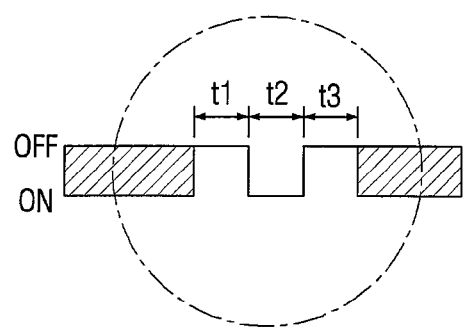
Figure 9B:
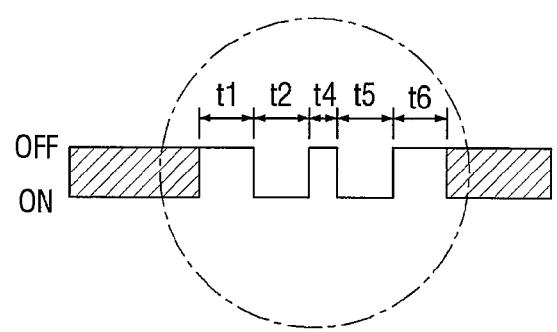

FIGS. 9A and 9B illustrate inputting patterns of the manipulation to select any one among the provided two options only with the one hand manipulation when the two options that are selected are provided to a user if one fingerprint sensor is operating. The signal pattern of FIG. 9A is uniform to the signal pattern of FIG. 8A. Regarding FIG. 9B, the illustrated timing graph indicates the two time sections in which the signals are on-stated during the total time sections in which the pattern is determined. For example, according to the pattern of FIG. 9B, the time section t4 is previously defined to be more than 0.2 seconds and less than 0.5 seconds, t5 be more than 0.3 seconds and less than 0.8 seconds, and t6 be more than 0.5 seconds.

Figure 10A:
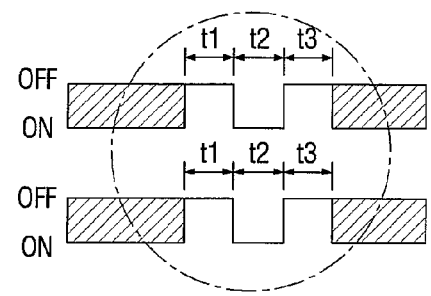
Figure 10B:
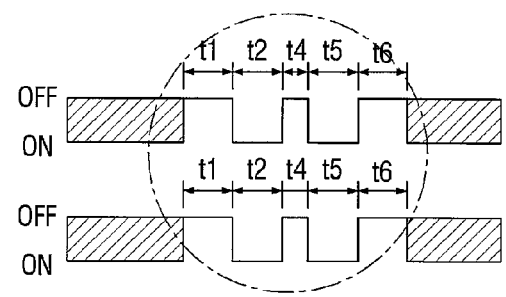
Figure 10C:
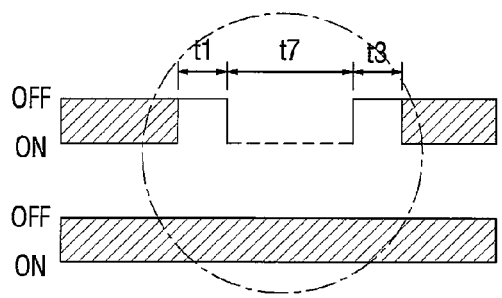
Figure 10D:
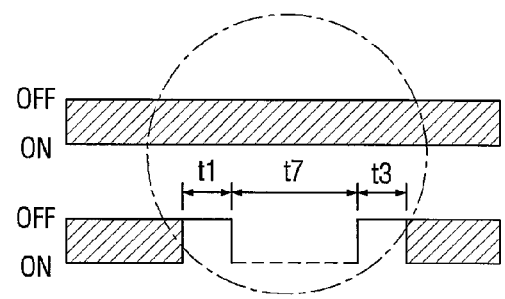

FIGS. 10A to 10D illustrate additional inputting patterns. FIG. 10A illustrates the pattern to simultaneously input the manipulation of FIGS. 8A and 8B with the both hands. FIG. 10B illustrates the pattern to simultaneously input the manipulation of FIG. 9B with the both hands. FIG. 10C is a timing graph indicating the manipulation of the left hand regarding a user grabbing the handgrip; a command according to the time when the singles are on-stated is inputted during the time section in which the pattern is determined. FIG. 10D is a timing graph indicating the manipulation of the right hand regarding a user grabbing the handgrip; a command according to the time when the signals are on-stated is inputted during the time section in which the pattern is determined. For example, according to the patterns of FIGS. 10C and 10D, the time section t7 is previously defined to be pattern that is inputted when exceeding 0.8 seconds.

FIGS. 11A, 11B, 11C, 11D, 11E, and 11F are diagrams describing examples in which the screen is converted with the user manipulation inputted according to this disclosure. Referring to FIG. 11A, the user identification information corresponding to the recognized fingerprints and corresponding additional information is displayed after entering into the body fat measuring mode. Further, a highlight reversing characters and shadows of arrows are displayed in order to display options that are changed. When the above screen is displayed, the first pattern of FIG. 8A corresponds to a command to decrease a setting value for one time, and the second pattern of FIG. 8B corresponds to a command to increase a setting value for one time.

Further, the third pattern of FIG. 10A corresponds to a command to move to next option among the listed options, and the fourth pattern of FIG. 10B corresponds to a command to move previous option among the listed options. Further, the fifth pattern of FIG. 10C corresponds to a command to increase gradually a setting value according to the time when the on-stated signals are inputted, and the sixth pattern of FIG. 10D corresponds to a command to decrease gradually a setting value according to the time when the on-stated signals are inputted.

Referring to FIG. 11A, when the first pattern is inputted while displaying the screen, the screen is converted into the screen of FIG. 11B in which the identification number is decreased by 1. On the contrary, when the second pattern is inputted, the screen is converted into the screen of FIG. 11C in which the identification number is increased by 1. When the third pattern is inputted while displaying the screen of FIG. 11A, the screen is converted into the screen of FIG. 11D in which next option setting the key is displayed. When the fourth pattern is inputted while displaying the screen of FIG. 11D, the screen is converted into the screen of FIG. 11A in which previous option setting the identification number is displayed. When the fifth pattern is inputted while displaying the screen of FIG. 11D, the screen of FIG. 11E in which 13 is increased according to the time when the on-stated signals are inputted is displayed. On the contrary, when the sixth pattern is inputted, the screen of FIG. 11F in which 17 is decreased according to the time when the on-stated signals are inputted is displayed.

Figure 12:
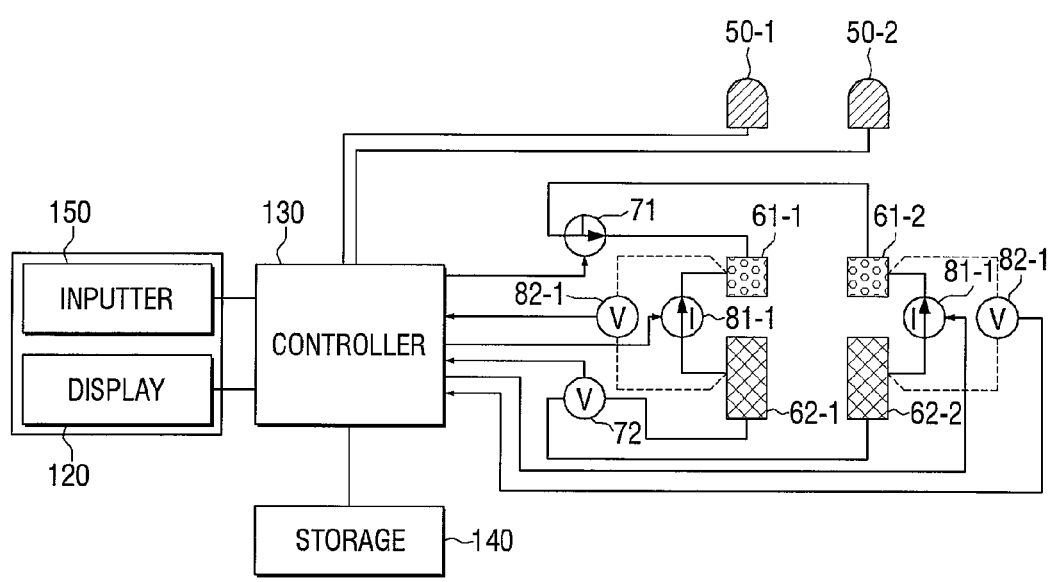
FIGS. 12 and 13 are circuit diagrams of an example refrigerator according to this disclosure.
Figure 13:
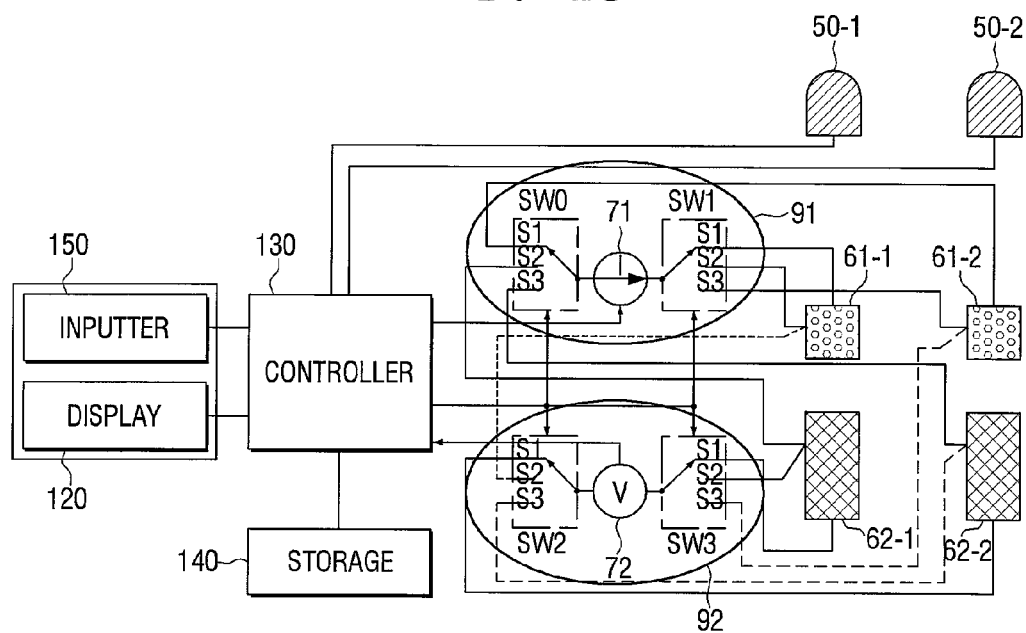

FIGS. 12 and 13 are example circuit diagrams of the refrigerator according to this disclosure. Referring to FIG. 12, the two electrical powers 81-1, 81-2 and the two voltage measurers 82-1, 82-2 are additionally included on the circuit by comparing the circuit diagram according to the embodiment of FIG. 5. Specifically, the left electrical power 81-1 and the voltage measurer 82-1 are connected to the current electrode 61-1 and the voltage electrode 62-1 of the left electrode 60-1 among a pair of the electrodes 60-1, 60-2, and the right electrical power 81-2 and the voltage measurer 82-2 are connected to the current electrode 61-2 and the voltage electrode 62-2 of the right electrode 60-2.

The added electrical powers 81-1, 81-2 provides and output the alternated currents to the user contacting hands through the two electrodes 61-1, 62-1 and/or 61-2, 62-2 of one handgrip. The added voltage measurer 82-1, 82-2 measures the voltage between the two electrodes 61-1, 62-1 and/or 61-2, 62-2 of one handgrip. The controller 130 measures the impedance of the hand regarding a user grabbing the handgrip from the provided alternated currents and the measured voltage. Further, the controller 130 determines whether a user properly grabs the handgrip by comparing the measured size of the impedance with a preset value.

Referring to FIG. 13, two switching units 91, 92 including four switching components (SW0, SW1, SW2, SW3) are included without including the additional electrical powers 81-1, 81-2 and the voltage measurers 82-1, 82-2 on the circuit when comparing with the circuit according to an embodiment of FIG. 12. The first switching unit 91 switches the connection to a pair of the electrodes which externally outputs the alternated currents provided from the electrical power 71 providing the alternated currents into the other electrodes. Specifically, the first switching unit 91 is connected between the outputting end of the electrical power 71 and a pair of the electrodes, and selects the two electrodes in which the alternated currents of the electrical power 71 will be outputted by the switching operation.

The first switching unit 91 includes the two switching components (SW0, SW1). Further, the first end of the first switching component (SW0) is connected to one end of the electrical power 71, the second end is connected to one side 61-1 among a pair of the current electrodes 61-1, 61-2, and the third and the fourth ends is connected to a pair of the voltage electrodes 62-1, 62-2. Further, the first end of the second switching component (SW1) is connected to another end of the electrical power 71, the second end is connected to the other side 61-2 among a pair of the current electrodes 61-1, 61-2, and the third and the fourth ends is connected to a pair of the voltage electrodes 62-1, 62-2.

The switching components (SW0, SW1) converts the connection between both ends of the electrical power 71 and the electrodes 61-1, 61-2, 62-1, 62-2 according to controlling signals of the controller 130. For one example, when the switching components are both first-stated (S1), both ends of the electrical power 71 and the current electrodes 61-1, 61-2 are connected to each other. When the switching components (SW0, SW1) are both second-stated (S2), both ends of the electrical power 71, the current electrode 61-1 and the voltage electrode 62-1 are connected to each other. When the switching components (SW0, SW1) are both third-stated (S3), both ends of the electrical power 71, the current electrode 61-2 and the voltage electrode 62-2 are connected to each other.

The second switching unit 92 switches the connection between both ends of the voltage measurer 72 measuring the voltage and a pair of the electrodes into the other electrodes. Specifically, the second switching unit 92 is connected between both ends of the voltage measurer 72 and a plurality of the electrodes, and the voltage measurer 72 selects the two electrodes of which the voltage will be measured by the switching operation.

The second switching unit 92 includes the two switching components (SW2, SW3). Further, the first end of the third switching component (SW2) is connected to one end of the voltage measurer 72, the second end is connected to one side 62-2 among a pair of the voltage electrodes 62-1, 62-2, the third end is connected to one side 61-1 among a pair of the current electrodes 61-1, 61-2, and the fourth end is connected to one side 62-2 among a pair of the voltage electrodes 62-1, 62-2. Further, the first end of the fourth switching component (SW3) is connected to the other end of the voltage measurer 72, the second end is connected to the other side 62-1 among a pair of the voltage electrodes 62-1, 62-2, the third end is connected to the other side 62-1 among a pair of the voltage electrodes 62-1, 62-2, and the fourth end is connected to the other side 61-2 among a pair of the current electrodes 61-1, 61-2.

The switching components (SW2, SW3) convert the connection between both ends of the voltage measurer 72 and the electrodes 61-1, 61-2, 62-1, 62-2 according to controlling signals of the controller 130. For one example, when the switching components (SW2, SW3) are both first-stated (S1), both ends of the voltage measurer 72 and the voltage electrodes 62-1, 62-2 are connected to each other. When the switching components (SW2, SW3) are both second-stated (S2), both ends of the voltage measurer 72, the current electrode 61-1 and the voltage electrode 62-1 are connected to each other. When the switching components (SW2, SW3) are both third-stated (S3), both ends of the voltage measurer 72, the current electrode 61-2, and the voltage electrode 62-2 are connected to each other. According to the above circuit constitution, the grabbing the handgrip is extracted without further including the additional electrical power and the voltage circuit.

Figure 14:
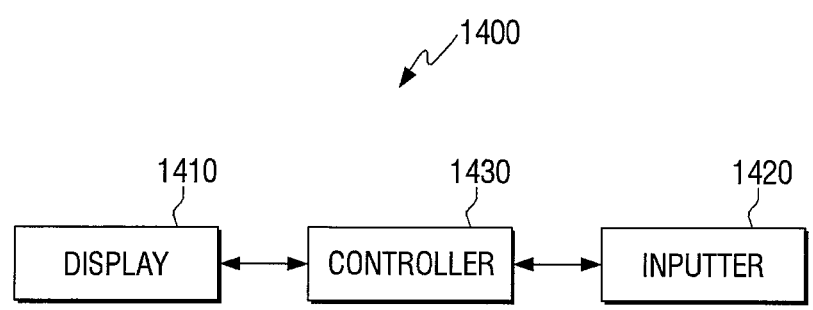
FIG. 14 is a block diagram of an example refrigerator according to this disclosure.

FIG. 14 is a block diagram of a refrigerator according to this disclosure. Referring to FIG. 14, the refrigerator 1400 includes the display 1410, the inputter 1420, and the controller 1430. The display 1410 displays screens. Specifically, the display 1410 may display the screen including characters to examine the eyesight of a user. For example, the characters or the numbers having preset sizes to examine the eyesight may be displayed on the screen. Further, pictures to examine the astigmatism, the retina disorder, and the color blindness as well as characters to examine the eyesight may be displayed on the screen of the display 1410. Further, the display 1410 may display the guide screen to separately examine the left eye and the right eye.

The inputter 1420 receives user inputting. Specifically, the inputter 1420 may receive inputting to confirm whether a user recognize the character from the displayed screen. For example, the inputter 1420 may be implemented to be microphone receiving the user voice. Further, the inputter 1420 may also be implemented to be buttons attached to the refrigerator 1400 or inputting device sensing the touch.

The controller 1430 controls each component of the refrigerator 1400. Specifically, the controller 1430 may control each component of the refrigerator 1400 to perform the eyesight measuring function in the refrigerator 1400. The controller 1430 may modify the screen of the display 1410 according to the received user inputting by the inputter 1420. Specifically, the controller 1430 may modify the character displayed on the screen of the display 1410 according to whether the user inputting corresponds to the character displayed on the screen. For example, when the number, 8, is displayed on the screen of the display 1410, and when the user voice speaking, "eight," is inputted through the inputter 1420, the controller 1430 analyzes the inputted user voice, determines that the received voice corresponds to the displayed character, and controls the display 1410 to modify and display the character at a higher eyesight level.

As described above, the refrigerator manages the eye health with more easy manipulation and convenient approach as home appliance to be viewed and used in every day at home.

Figure 15:
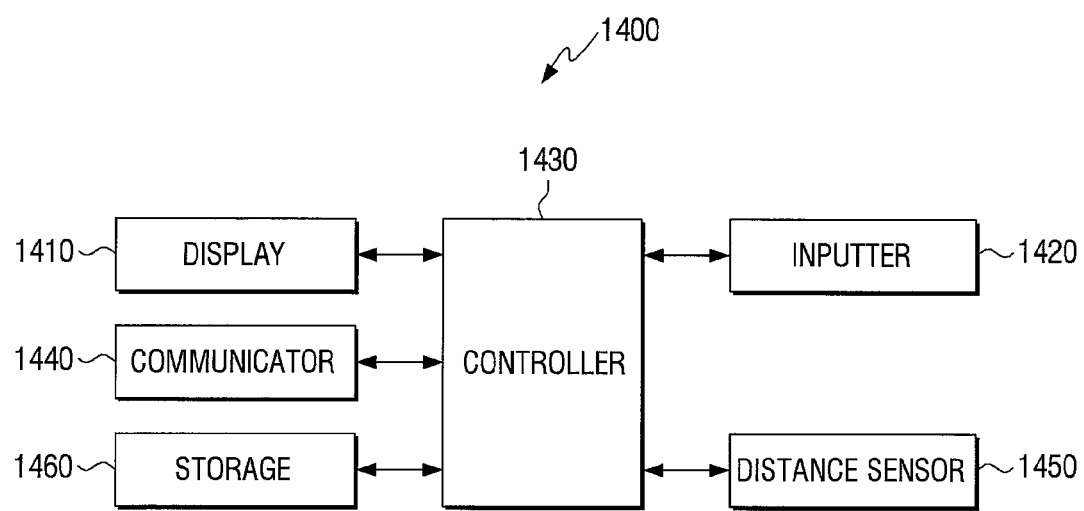
FIG. 15 is a block diagram of an example refrigerator according to this disclosure.

FIG. 15 is a block diagram of a refrigerator according to this disclosure. Referring to FIG. 15, the refrigerator 1400 includes the display 1410, the inputter 1420, the controller 1430, a communicator 1440, a distance sensor 1450, and the storage 1460. Herein, specific constitution and operation of the display 1410, the inputter 1420, and the controller 1430 includes the above descriptions regarding the display 1410, the inputter 1420, and the controller 1430 of FIG. 14, which will not be further explained regarding the overlapping.

The communicator 1440 performs communication with external devices. Specifically, the communicator 1440 may be connected to a terminal apparatus that can be carried by a user or the home network built within the house. Further, the communicator 1440 may receive signals corresponding to the character inputted by a user on the terminal apparatus from the external terminal apparatus. Further, the communicator 1440 may perform communication with the user terminal apparatus connecting to a home server of the home network.

Communication methods supported by the communicator 1440 may be performed according to various standards such as Wi-Fi, Bluetooth, Zigbee, IrDA, and RF (radio frequency), wire communication, or the like. Further, the communicator 1440 may perform communication connecting to the home server of the internet network passing through communication networks such as CDMA, WCDMA, GSM, EPC (evolved packet core), LTE (long term evolution), or the like.

The distance sensor 1450 senses the distance from a user. Specifically, the distance sensor 1450 may include a light-emitting component and a light-receiving component, and calculate the distance by measuring the time taken for the emitting light to reflect from a user and come back.

The storage 1460 stores one or a plurality of pieces of user information, and store eyesight measuring information respectively corresponding to the user information. Further, the storage 1460 may store the screens to be displayed for the eyesight measuring and the algorithms calculating for the eyesight. The storage 1460 may store the implementing programs downloaded or installed from the external server.

The controller 1430 may determine whether the displayed character corresponds to the signals corresponding to the character inputted through the communicator 1440, and modify the screen to be displayed on the display 1410. Further, the controller 1430 may control the display 1410 to display the screen requesting the adjusting the distance by using the distance sensed by the distance sensor 1450 when the distance of a user from the refrigerator 1400 is determined to be shorter or longer insufficiently for the measuring eyesight.

The controller 1430 may calculate the user eyesight according to the algorithms calculating the eyesight and store the calculated eyesight information on the storage 1460 by matching with the inputting or identified user information.

As described above, the refrigerator manages the eye health with more easy manipulation and convenient approach as home appliance to be viewed and used in every day at home.

Figure 16:
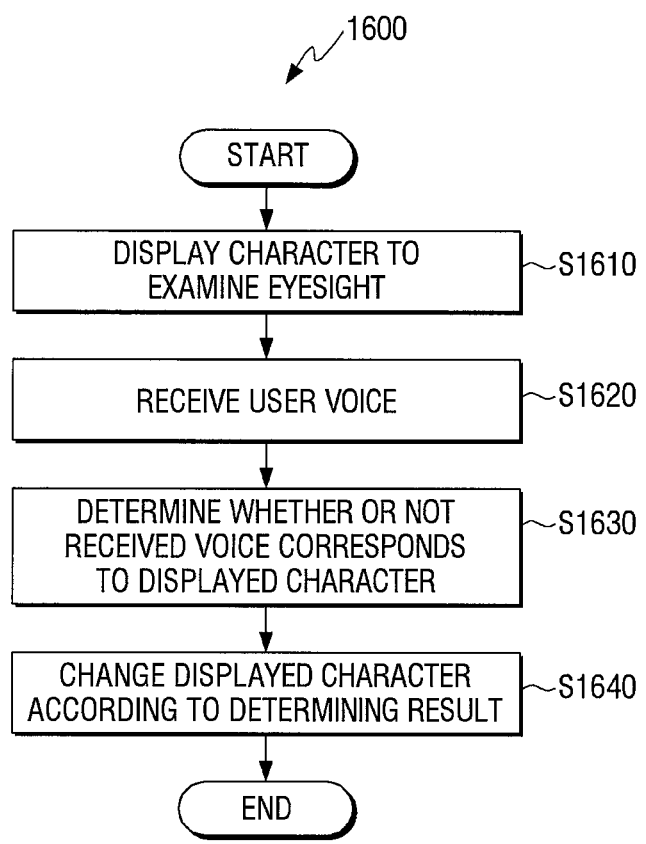
FIG. 16 is an example method for measuring body composition according to this disclosure.

FIG. 16 is a flowchart provided to explain an example body composition measuring method 1600 according to this disclosure. Referring to FIG. 16, the character to measure the eyesight is displayed at S1610. Specifically, the refrigerator may display the character having a preset size per certain eyesight level in order to measure the eyesight. At S1620, the user voice is received. Specifically, the refrigerator may receive the voice spoken by a user who is displaced by certain distance in order to measure the eyesight. At S1630, the received voice is determined to correspond to the displayed character. Specifically, the refrigerator may determine whether the voice corresponds to the speaking of the displayed character by analyzing the received voice. At S1640, the character is changed according to the determining result at S1630. Specifically, when the analyzed voice is determined to correspond to the displayed character, the refrigerator may modify and display the character having a smaller size at a higher eyesight level.

As described herein, the body composition measuring method manages the eye health with more easy manipulation at the refrigerator which enhances the user approaches.

Further, the body composition measuring method according to an embodiment can be implemented in the refrigerator of FIGS. 14 and 15. Further, the described body composition measuring method can be implemented to be at least one program, and such program is stored in computer readable recording medium.

FIG. 17 is a flowchart specifically describing an example body composition measuring method 1700 according to this disclosure. Referring to FIG. 17, a user is determined to be registered at S1705. Specifically, the refrigerator may recognize the user fingerprints applied to the above embodiment or determine whether a user is registered through another user inputting. When a user is not registered at S1705: N, new registering to store identification information regarding a user is performed at S1710.

When a user is registered at S1705: Y, a corresponding user is selected at S1715 among the previously registered users. Specifically, the refrigerator may provide the unique identification numbers or the name list regarding the registered users. At S1720, the screen for measuring the eyesight is displayed. Specifically, the refrigerator may display the screen including the character having a preset size corresponding to the specific eyesight level. At S1725, the user voice is received. Specifically, the refrigerator may receive the user voice which recognizes or does not recognize the displayed character. At S1730, the meaning of the received voice is determined to be uniform to the meaning of the displayed character. Specifically, the refrigerator may determine whether the received voice corresponds to the displayed character by analyzing the received voice. When the two meanings are not uniform to each other at S1730: N, the refrigerator modifies the screen including the character corresponding to a lower eyesight level than the eyesight level corresponding to the displayed character at S1735. Further, the refrigerator displays the screen including the character at the changed level at S1720. When the two meanings are uniform to each other at S1730: Y, the refrigerator determines whether the number to correctly speak the displayed characters by a user is more than a threshold (Th) at S1740.

When the correctly speaking number is less than a threshold (Th), the refrigerator modifies the screen including the character corresponding to a higher eyesight level than the eyesight corresponding to the displayed character at S1745. Further, the refrigerator displays the screen including the character at the changed level at S1720. When the correctly speaking number comes to be more than a threshold (Th) at S1740: Y, the user eyesight is calculated at S1750. Specifically, the refrigerator may calculate the user eyesight according to the prestored algorithms calculating the eyesight from the displayed characters, the characters correctly spoken by a user, and the characters incorrectly spoken by a user. At S1755, the calculating result at S1750 is displayed and stored. Specifically, the refrigerator may display the eyesight calculating result to a user, and store the examining result on the storage by matching with the user identification information.

The body composition measuring method using the refrigerator manages the eye health with more easy manipulation in the refrigerator which enhances the user approaches. Further, the body composition measuring method according to an embodiment can be implemented to be in the refrigerator of FIGS. 14 and 15. Further, the body composition measuring method can be implemented to be at least one program performing the measuring body composition, and such program may be stored in computer readable recording medium.

The non-transitory computer readable medium does not mean a medium storing data for a short period such as a register, a cash, a memory, or the like, but means a machine-readable medium semi-permanently storing the data. Specifically, various applications or programs described above is stored and provided in the non-transitory computer readable medium such as a compact disc (CD), a digital versatile disk (DVD), a hard disk, a Blu-ray disk, a universal serial bus (USB), a memory card, a read-only memory (ROM), or the like.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A refrigerator, comprising:
a handgrip;
a fingerprint sensor configured to sense a fingerprint;
a body composition measurer configured to measure a body composition;
a display; and
a controller configured to:
when a user touches the fingerprint sensor, control the fingerprint sensor to sense the fingerprint of the user,
when a touch of the fingerprint sensor is maintained for a predetermined time after touching the fingerprint sensor, control the body composition measurer to measure the body composition of the user and control the display to display the measured body composition, and
recognize the user based on the sensed fingerprint and store the measured body composition to information corresponding to the recognized user in a storage.

2. The refrigerator of claim 1, wherein the fingerprint sensor is provided with a contact surface to sense the fingerprint of a thumb within an operating range where the thumb of a hand can reach the handgrip when the user grips the handgrip.

3. The refrigerator of claim 1, wherein the body composition measurer is provided with a pair of electrodes spanning portions of the handgrip in contact with palms of both hands when the user grips the handgrip with his or her both hands.

4. The refrigerator of claim 1, wherein the refrigerator is a side by side (SBS) door type, wherein the handgrip is provided on both side doors, and a pair of electrodes is arranged on both handgrips so as to be contacted by two hands of the user gripping the handgrips of the side doors.

5. The refrigerator of claim 1, wherein the controller is configured to control the body composition measurer to measure the body composition when prestored identification information regarding the user corresponding to the sensed fingerprint is searched.

6. The refrigerator of claim 1, wherein the body composition measurer is configured to measure an impedance of a hand by outputting alternating currents to the hand of the user gripping the handgrip, and wherein the controller is configured to determine whether or not the user grips the handgrip is properly based on a measured size of the impedance.

7. The refrigerator of claim 1, wherein the body composition measurer further comprises:
a power source configured to provide alternating currents to measure the body composition; and
a switching unit configured to switch connection to a pair of electrodes outputting the provided alternating currents externally and to other electrodes.

8. The refrigerator of claim 1, wherein the controller is configured to control selecting options provided to the user according to patterns of a signal of the fingerprint being sensed by the fingerprint sensor.

9. The refrigerator of claim 1, wherein the controller is configured to select options provided to the user according to a pattern of impedance in which the impedance of a hand contacting at least one electrode among a pair of the electrodes in the body composition measurer changes.

10. The refrigerator of claim 1, wherein the storage is further configured to store additional information comprising at least of an age, a gender, a height, and a weight regarding a plurality of users, wherein the controller is configured to search additional information that corresponds to the recognized user among a plurality of pieces of the stored additional information, and wherein the body composition measurer is configured to measure the body composition of the user by considering the searched additional information.

11. The refrigerator of claim 1, wherein the display is configured to display characters to examine an eyesight of the user.

12. The refrigerator of claim 11, further comprising:
an inputter configured to receive a user voice, wherein the controller is configured to change a character displayed on the display according to whether the received user voice corresponds to the displayed character.

13. A method to measure a body composition, the method comprising:
sensing a fingerprint of a user when the user touches a handgrip of a refrigerator;
recognizing the user based on the sensed fingerprint;
measuring the body composition of the user when a touch of the handgrip is maintained for a predetermined time after touching the handgrip; and
storing the measured body composition to information corresponding to the recognized user.

14. The method of claim 13, wherein the measuring the body composition comprises measuring the body composition of the user when a prestored identification information of the user corresponding to the sensed fingerprint is searched.

15. The method of claim 13, further comprising:
switching a connection of a power source providing alternated currents to measure the body composition with a pair of electrodes outputting the provided alternating currents externally to connection with other electrodes.

16. The method of claim 13, further comprising:
previously storing additional information comprising at least one of an age, a gender, a height, and a weight regarding a plurality of users; and
searching additional information corresponding to the recognized user among a plurality of pieces of the stored additional information, wherein the measuring the body composition comprises analyzing the body composition of the user as a function of the searched additional information.

17. The method of claim 13, further comprising:
displaying a character to examine an eyesight of the user;
receiving a user voice; and
changing the displayed character according to whether or not the received user voice corresponds to the displayed character.

* * * * *